United States Patent [19]

Campopiano et al.

[11] Patent Number: 5,157,119
[45] Date of Patent: Oct. 20, 1992

[54] PROCESS FOR PREPARING SULFONYLUREAS

[75] Inventors: Onorato Campopiano, Newark; Marcus P. Moon, Wilmington, both of Del.

[73] Assignee: E. I. Du Pont de Nemours and Company, Wilmington, Del.

[21] Appl. No.: 838,164

[22] Filed: Feb. 20, 1992

Related U.S. Application Data

[62] Division of Ser. No. 776,138, Oct. 15, 1991.

[51] Int. Cl.⁵ .................. C07D 239/69; C07D 239/48; C07D 251/42; C07D 251/52

[52] U.S. Cl. .................. 544/211; 544/206; 544/208; 544/321; 544/323

[58] Field of Search ............... 544/211, 206, 208, 321, 544/323

[56] References Cited

U.S. PATENT DOCUMENTS 4,546,179 10/1985 Kunz .................. 544/206

Primary Examiner—John M. Ford

[57] ABSTRACT

This invention relates to a process for the preparation of a benzene sulfonylurea herbicide by reacting a sulfonyl chloride with a cyanate salt in the presence of a heterocyclic amine, a base and a solvent.

13 Claims, No Drawings

PROCESS FOR PREPARING SULFONYLUREAS

This is a division of application Ser. No. 07/776,138, filed Oct. 15, 1991 pending.

FIELD OF THE INVENTION

This invention is directed to a base-accelerated cyanate process for the preparation of sulfonylurea herbicides.

STATE OF THE ART

Sulfonylurea herbicides are an extremely potent class of herbicides discovered relatively recently which generally consist of a sulfonylurea bridge, —SO$_2$NHCONH—, linking two aromatic or heteroaromatic ring structures. Such herbicides have become commercially important. There is therefore a continuing need to discover new processes for their preparation that offers advantages that add to their commercial desirability.

U.S. Pat. No. 4,546,179 discloses the preparation of sulfonylurea herbicides via a cyanate route. EP-A-336,587, and references cited therein, disclose 2,6-disubstituted sulfonylureas.

SUMMARY OF THE INVENTION

This invention pertains to a process for the preparation of sulfonylureas of Formula I comprising reacting a sulfonyl chloride of Formula III with a cyanate salt of Formula IV in the presence of heterocyclic amine of Formula V and a base acording to Equation 1

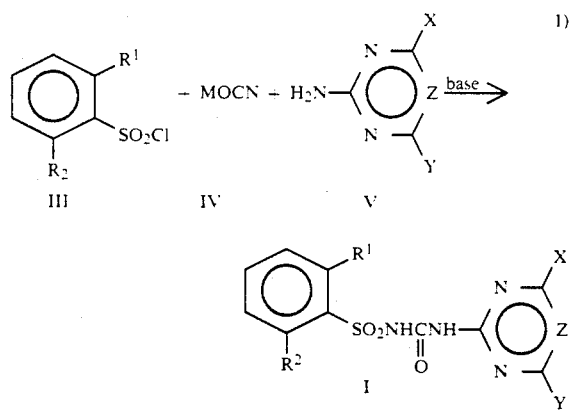

wherein
R$^1$ is selected from the group CO$_2$R$^3$ and CHFCH$_3$;
R$^2$ is selected from the group CH$_3$, CH$_2$CN and Cl;
R$^3$ is selected from the group C$_1$-C$_3$ alkyl;
M is selected from the group Na, K and NH$_4$;
X is selected from the group CH$_3$ and N(CH$_3$)$_2$;
Y is selected from the group CH$_3$, OCH$_3$ and OCH$_2$CF$_3$; and
Z is selected from the group CH and N.

This invention further pertains to intermediates of Formula II

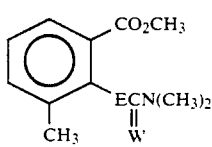

wherein
E is selected from the group O and S; and
W is selected from the group O and S;
provided that E and W are not simultaneously O or S.

The compounds of Formula II are useful to prepare the compounds of Formula III used in the process of preparing the compounds of Formula I.

In the above recitations, C$_1$-C$_3$ alkyl denotes methyl, ethyl, propyl and isopropyl.

Typical reaction conditions are as follows. The solvent is selected from aprotic solvents with preferred solvents selected from acetonitrile, acetone, dioxane, methylene chloride, tetrahydrofuran and suitable combinations thereof. The most preferred solvent is acetonitrile. Temperatures are 0° to 50° C. Preferred temperatures are 20° to 30° C. Reaction pressures are 1 to 5 atmospheres. The preferred pressure is 1 atmosphere. Reaction times are 0.1 to 24 hours, preferably 1 to 3 hours. The bases are selected from pyridine, picoline, lutidine, sodium bicarbonate, sodium carbonate, sodium acetate and combinations thereof. The preferred base is pyridine. Preferred mole ratio of the compound of Formula III to base is 1:0.5 to 1:2.

Specifically preferred processes for the greatest utility of their products are:

1) The process of Equation 1 wherein R$^1$ is CO$_2$R$^3$, R$^2$ is CH$_3$, R$^3$ is CH$_3$, Z is N, X is N (CH$_3$)$_2$ and Y is OCH$_2$CF$_3$.
2) The process of Equation 1 wherein R$^1$ is CO$_2$R$^3$, R$^2$ is Cl, R$^3$ is CH(CH$_3$)$_2$, Z is CH and X and Y are CH$_3$.
3) The process of Equation 1 wherein R$^1$ is CHFCH$_3$, R$^2$ is Cl, Z is N, X is CH$_3$ and Y is OCH$_3$.
4) The process of Equation 1 wherein R$^1$ is CO$_2$R$^3$, R$^2$ is CH$_2$CN, R$^3$ is CH$_3$, Z is CH and X and Y are CH$_3$.

The sulfonyl chlorides of Formula III are either known or can be prepared by various methods known to one skilled in the art. For example, the compounds of Formula III can be prepared by i) oxidative chlorination of thioethers such as taught in Recl. Trav. Chim. Pays-Bas 101, 91 (1982), ii) diazotization of aromatic amines with sodium nitrite in hydrochloric acid, followed by reaction of the resulting diazonium salt with sulfur dioxide and cuprous chloride as described in J. Org. Chem., 1824 (1960), iii) heteroatom-facilitated lithiation, followed by sulfonation as taught in EP-A-73,562 and reviewed in Org. Reactions, 26 1 (1979).

In addition, sulfonyl chlorides of Formula III can be prepared from substituted phenols via a Newman rearrangement (See J. Org. Chem., 31, 3980 (1966) as illustrated below in Scheme 1.

Scheme 1

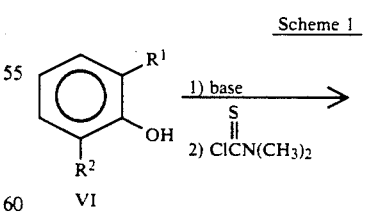

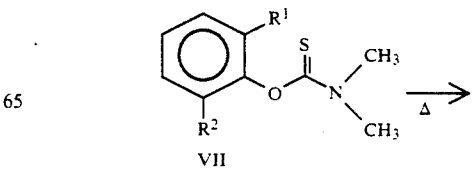

-continued
Scheme 1

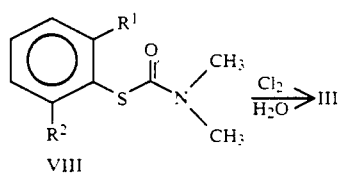

The phenol VI is reacted with a base such as sodium or potassium hydroxide or sodium hydride in an appropriate solvent such as a lower alcohol or inert aprotic solvent followed by treatment with a dialkyl thiocarbamoyl chloride to form a thiocarbamate of Formula VII (See *Syn. Comm.*, 17, 1761 (1987)). The thiocarbamate VII, which need not be isolated, is heated at temperatures of 100°-250° C., neat or dissolved in an appropriate solvent, such as o-dichlorobenzene, to effect rearrangement to VIII. Compounds of Formula VIII are readily converted to the sulfonyl chloride derivative III by reaction with chlorine gas in the presence of water or alternatively by action of aqueous sodium hypochlorite with acid.

The amines of Formula V are also either known or can be prepared by methods known in the art. For example, see "The Chemistry of Heterocyclic Compounds," Vol. 13 and 16, Interscience Publishers, Inc., New York and "The Chemistry of the Amino Group," Edited by S. Patai.

Interscience Publishers, Inc., 1968, pages 37-77.

The process of this invention is best carried out in a solvent such as acetonitrile, dioxane, methylene chloride, tetrahydrofuran, or combinations thereof. The preferred solvent for greater reactivity and ease of handling is acetonitrile, when an alkali metal cyanate is used.

The cyanate salts IV are ammonium, sodium or potassium. Preferred for greater reactivity and availability are sodium and potassium cyanate. The reaction temperature is in the range of 0° to about 50° C., with ambient temperature preferred for ease of operation. The reaction pressure is 1 to 5 atmospheres, with 1 atmosphere preferred.

The reaction time is determined by the reactivity of the starting materials. In some cases, the reaction is complete after a few minutes while in other cases a reaction time up to about 24 hours is advantageous. The preferred reaction time is normally in the range of 1 to 3 hours.

The relative ratio of reactants is determined by their relative cases and reactivity. The sulfonyl chloride (III) and heterocyclic amine (V) are normally used in about a 1:1 to 1.2:1 mole ratio. The cyanate salt is used in excess. Mole ratios of sulfonyl chloride to cyanate salt can be 1:1 to 1:10 with 1:2 preferred for reasons of ease of operation and efficiency.

The mole ratio of sulfonyl chloride to base is generally 1:0.1 to 1:3, with 1:0.5 to 1:2 preferred and 1:1 to 1:2 being most preferred. Amounts of base less than the minimum indicated will produce Compound I but the yield will be reduced an /or longer reaction times will result. The bases are selected from pyridine, picoline, lutidine, sodium bicarbonate, sodium carbonate, sodium acetate and combinations thereof, with pyridine as the preferred base. The base accelerates the reaction and significantly improves the yield and ease of isolation of the final product.

The resulting sulfonylurea can be isolated by several methods depending on the solvent, the solubility of the product and the presence of by-products. In some cases, the reaction can be diluted with water, acidified and filtered to give essentially pure sulfonylurea. In other cases, the product can be dissolved in dilute base, filtered, and the filtrate acidified to reprecipitate the product. In still other cases, the product is recrystallized to yield a purified product.

The process of this invention is further illustrated by the following examples.

EXAMPLE 1

Preparation of methyl 2-(chlorosulfonyl)-3-methyl benzoate

A mixture of 12 g of KOH pellets, 150 mL of methanol and 24.9 g of methyl 2-hydroxy-3-methylbenzoate (I) was stirred at room temperature for 0.5 hours. The mixture was then cooled to 5° C. and 19 g of dimethylthiocarbamoyl chloride was added in one portion. An exotherm of 5° C. was observed. The resulting mixture was stirred for 2 hours and then added to 300 mL of ice water. After filtering, the crystalline product was washed with water and oven dried to yield 30-35 g of methyl 2-[(dimethyl-amino)thioxomethoxy]-3-methylbenzoate II, (E is O, W is S) in 80-92% yield, mp 94-96° C.

$^1$H NMR (300 MHz, CDCl$_3$) δ2.30 (s, 3H), 3.50 (d, 6H), 3.85 (s, 3H), 7.25 (m, 1H), 7.45 (d, 1H), 7.85 (d, 1H). Mass Spec m/e: 253 (m$^+$), 220, 194, 149, 121, 88

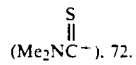
(Me$_2$NC$^-$), 72.

In a reaction flask equipped for stirring was charged 15 g of the product above and 100 mL o-dichlorobenzene. It was heated to reflux under nitrogen atmosphere for 18 hours overnight to effect the Newman-Kwart rearrangement to II (E is S, W is O). The rearrangement was complete as determined by GC analysis. The structure of the product II (E is S, W is O) was identified by GC/MS, m/e: 253 (m$^+$), 220, 194, 149, 121, 77, 72

(Me$_2$NC$^-$).

The absence of 88

(Me$_2$NC$^+$)

indicates a complete rearrangement. The same reaction can be carried out without solvent by heating the solids directly in a silicone oil bath at 220° C. for 6 hours to effect the Newman-Kwart rearrangement to II (E is S, W is O). The rearrangement can be monitored by GC. The rearranged product was characterized by $^1$H NMR (300 MHz, CDCl$_3$) δ2.50 (s, 3H), 3.10 (br.d, 6H), 3.90 (s, 3H), 7.35 (m, 1H), 7.42 (m, 1H), 7.60 (m, 1H) and by GC/MS, m/e: 253 (m+), 220, 194, 149, 121, 77, 72

(Me$_2$NC$^-$).

The above rearranged product in o-dichlorobenzene was added 100 mL H₂O and chlorinated at 20° C. A total of 20.7 g chlorine was charged over one hour. After stirring for another hour, the organic layer was rotovapped under vacuum to yield an orange liquid which crystallized upon cooling. It was worked up by dissolving in 100 mL methanol and then chilled in dry ice-acetone bath to crystallize. Filtration and drying afforded 9.7 g of white crystals (65%) yield which was identified to be methyl 2-(chlorosulfonyl)-3-methylbenzoate, mp 115°-116° C.

¹H NMR (CDCl₃) δ2.80 (s, 3H), 3.90 (s, 3H), 7.35 (d, 1H), 7.45 (d, 1H), 7.60 (t, 1H). m/e=248.

EXAMPLE 2

Preparation of Methyl 2-nitro-3-methylbenzoate

Thionylchloride (253 mL) was added dropwise to 3 l methanol at 0°-10° C. Toward end of the addition, the temperature was allowed to rise to 20° C. Solid 2-nitro-3-methylbenzoic acid (500 g) was charged in one portion and the reaction mixture was heated to reflux overnight. It was distilled until pot reached 73° C. After cooling to 60° C., 685 mL water was introduced dropwise and the reaction mixture was cooled to 20° C. Upon adding 26 mL water and 125 mL 80% NaOH, the pH was adjusted to 7. The product was collected by filtration and washed with 3×100 mL water and air dried overnight. Yield of methyl 2-nitro-3-methylbenzoate was 503.5 g (93.5%), mp 72° C.

¹H NMR (300 MHz, CDCl₃) δ2.38 (s, 3H), 3.90 (s, 3H), 7.50 (m, 2H), 7.88 (m, 1H).

EXAMPLE 3

Preparation of Methyl 2-benzylthio-3-methylbenzoate

In a 5 l pot was charged 483 g of methyl 2-nitro-3-methylbenzoate, 319 g benzyl mercaptan and 100 mL dimethyl formamide. Upon cooling to 0° C., a solution of 321 g potassium tert-butoxide in 1500 mL dimethyl formamide was added dropwise over 2.5 hours at 0°-5° C. The reaction mixture was stirred at 0° C. for 1.5 hours and then at room temperature overnight. The reaction was quenched by addition of 1 l water and worked up by extraction with 2 l methylene chloride. Upon washing with water (3×1 l), the methylene chloride layer was dried over MgSO₄, filtered and rotovapped to give 517 g of crude methyl 2-benzylthio-3-methylbenzoate (77% yield) as a liquid.

¹H NMR (300 MHz, CDCl₃) δ2.30 (s, 3H), 3.90 (s, 3H), 3.95 (s, 2H), 7.10-7.40 (m, 8H).

EXAMPLE 4

Preparation of Methyl 2-(chloro-sulfonyl)-3-methyl benzoate

Chlorine gas (542 g) was fed into a solution of methyl 2-benzylthio-3-methylbenzoate (417 g), methylene chloride (2 l) and water (1 l) over 5.5 hours at 20°-25° C. Upon complete addition, the reaction mixture was stirred at room temperature for another hour and then allowed to stand overnight. After phase cut, the organic layer was solvent exchanged into hexanes on rotovap. Upon cooling, the solids were filtered and washed with hexanes. After air drying, 179 g of methyl 2-(chlorosulfonyl)-3-methylbenzoate were obtained, mp 114°-116° C.

¹H NMR (300 MHz, CDCl₃) δ2.80 (s, 3H), 3.90 (s, 3H), 7.35 (d, 1H), 7.45 (d, 1H), 7.60 (t, 1H).

EXAMPLE 5

Preparation of Methyl 2-[[[[[4-(dimethylamino)-6-(2,2,2-trifuloroethoxy)-1,3,5-triazin-2-yl]amino]carbonyl]amino]sulfonyl]-3-methylbenzoate To a stirred mixture of 26.3 g (0.41 moles) of sodium cyanate and 33 mL of pyridine (0.4 moles) in 670 mL of acetonitrile was added 47.4 g (0.2 moles) of 4-(dimethylamino)-6-(2,2,2-trifluoroethoxy)-1,3,5-triazin-2-amine, followed by 60.31 g (0.24 moles) of methyl-2-(chlorosulfonyl)-3-methyl benzoate in one portion. Upon addition of the sulfonyl chloride an endotherm occurred. The reaction flask was immersed in a water bath, the reaction mixture stirred for 2.3 hours and then poured into about 1.5 L of ice water while stirring. Concentrated HCl (36%) was added in portions to bring the pH of the mixture from an initial 6 to 1. The solids were collected by filtration and the filter cake washed repeatedly with 20 mL portions of methanol. The solid was dried over 3 days in a vacuum oven at 40° C. to yield 65.18 g of an off white solid (65%), mp 104°-110° C. Melting points of this material have been seen to be widely variable depending on mode of synthesis, crystallization solvent, and degree of hydration. A more reliable criterion of purity is ¹H-NMR and LC.

¹H NMR (300 MHz, CDCl₃) δ12.40 (s, 1H, N—$\underline{H}$), 7.5 (m, 1H, aromatic), 7.4-7.2 (m, 2H, aromatic), 7.10 (s, 1H, N—$\underline{H}$), 4.74 (q, 2H, $\underline{CH_2}CF_3$), 3.9 (s, 3H, OCH₃), 3.21 (s, 6H, N(CH₃)₂, 2.95 (s, 3H, C—CH₃).

The purity of the above product was determined by LC to be 97.2%.

A sample of the above sulfonylurea (1 g) was slurried in 10 ml methanol at room temperature. Upon adding 0.5 g of 25% NaOMe solution, a clear solution formed which crystallized again after a few minutes. The crystals were filtered and dried in vacuum oven at 40° C. overnight to give 0.9 g of the sodium salt of sulfonylurea. The purity of the salt was determined by LC to be 99.6%.

The process of the present invention produces compounds useful as herbicides. Compounds of Formula I are herbicidal. Compounds of Formula I can be isolated in two crystal forms. Thus the process of this invention includes the preparation of either or both crystal forms of compounds of Formula I.

What is claimed is:

1. A process for preparing sulfonylurea compounds of the Formula I

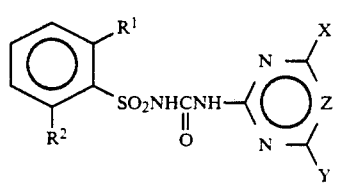

said process comprising reacting a sulfonyl chloride of Formula III

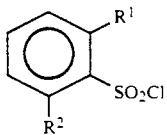

with a cyanate salt of the Formula IV

MOCN      IV in the presence of a heterocyclic amine of the Formula V

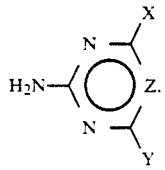

0.1 to 3 mols of base per mol of sulfonyl chloride of Formula III, the base being selected from pyridine, picoline, lutidine, sodium bicarbonate, sodium carbonate, sodium acetate and combinations thereof and an aprotic solvent at a temperature of from 0° to 50° C. and a pressure of from 1 to 5 atmospheres; wherein
$R^1$ is selected from the group $CO_2R^3$ and $CHFCH_3$;
$R^2$ is selected from the group $CH_3$, $CH_2CN$ and Cl;
$R^3$ is selected from the group $C_1$–$C_3$ alkyl;
M is selected from the group Na, K and $NH_4$;
X is selected from the group $CH_3$ and $N(CH_3)_2$;
Y is selected from the group $CH_3$, $OCH_3$ and $OCH_2CF_3$; and
Z is selected from the group CH and N.

2. The process of claim 1 wherein the amount of base is 0.5 to 2 mols per mol of sulfonyl chloride of Formula III, the temperature is 20° to 30° C. and the pressure is one atmosphere.

3. The process of claim 2 wherein $R^1$ is $CO_2R^3$;
$R^2$ is $CH_3$;
$R^3$ is $CH_3$;
Z is N;
X is $N(CH_3)_2$; and
Y is $OCH_2CF_3$.

4. The process of claim 2 wherein
$R^1$ is $CO_2R^3$;
$R^2$ is Cl;
$R^3$ is $CH(CH_3)_2$;
Z is CH;
X is $CH_3$; and
Y is $CH_3$.

5. The process of claim 2 wherein
$R^1$ is $CHFCH_3$;
$R^2$ is Cl;
Z is N;
X is $CH_3$; and
Y is $OCH_3$.

6. The process of claim 2 wherein
$R^1$ is $CO_2R^3$;
$R^2$ is $CH_2CN$;
$R^3$ is $CH_3$;
Z is CH; and
X and Y are $CH_3$.

7. The process of claim 3 wherein
M is selected from Na or K;
the solvent is acetonitrile; and
the base is pyridine.

8. The process of claim 1 wherein the base is pyridine.

9. The process of claim 2 wherein the base is pyridine.

10. The process of claim 3 wherein the base is pyridine.

11. The process of claim 1 wherein the solvent is selected from acetonitrile, dioxane, methylene chloride, tetrahydrofuran and combinations thereof.

12. The process of claim 11 wherein the solvent is acetonitrile.

13. The process of claim 12 wherein the cyanate salt of Formula IV is selected from sodium cyanate and potassium cyanate.

* * * * *

UNITED STATES PATENT AND TRADEMARK OFFICE
CERTIFICATE OF CORRECTION

PATENT NO. : 5,157,119

DATED : October 20, 1992

INVENTOR(S) : Campopiano et al.

It is certified that error appears in the above-identified patent and that said Letters Patent is hereby corrected as shown below:

On cover page, column 1, after [75] Inventors: delete Marcus P. Moon. The sole inventor is Onorato Campopiano of Newark, Delaware.

Column 5, line 36, "In a 5 1 pot was charged 483 g of methyl 2-nitro-3-" should read --In a 5 L pot was charged 483 g of methyl 2-nitro-3- --.

Column 5, line 43, "reaction was quenched by addition of 1 1 water and" should read --reaction was quenched by addition of 1 L water and--.

Column 5, line 44, "worked up by extraction with 2 1 methylene chloride." should read --worked up by extraction with 2 L methylene chloride.--

Column 5, line 45, "Upon washing with water (3X11) the methylene chlo-" should read --Upon washing with water (3X1L) the methylene chlo- --.

Signed and Sealed this

Twenty-sixth Day of October, 1993

*Attest:*

BRUCE LEHMAN

*Attesting Officer*   Commissioner of Patents and Trademarks